Figure 1:
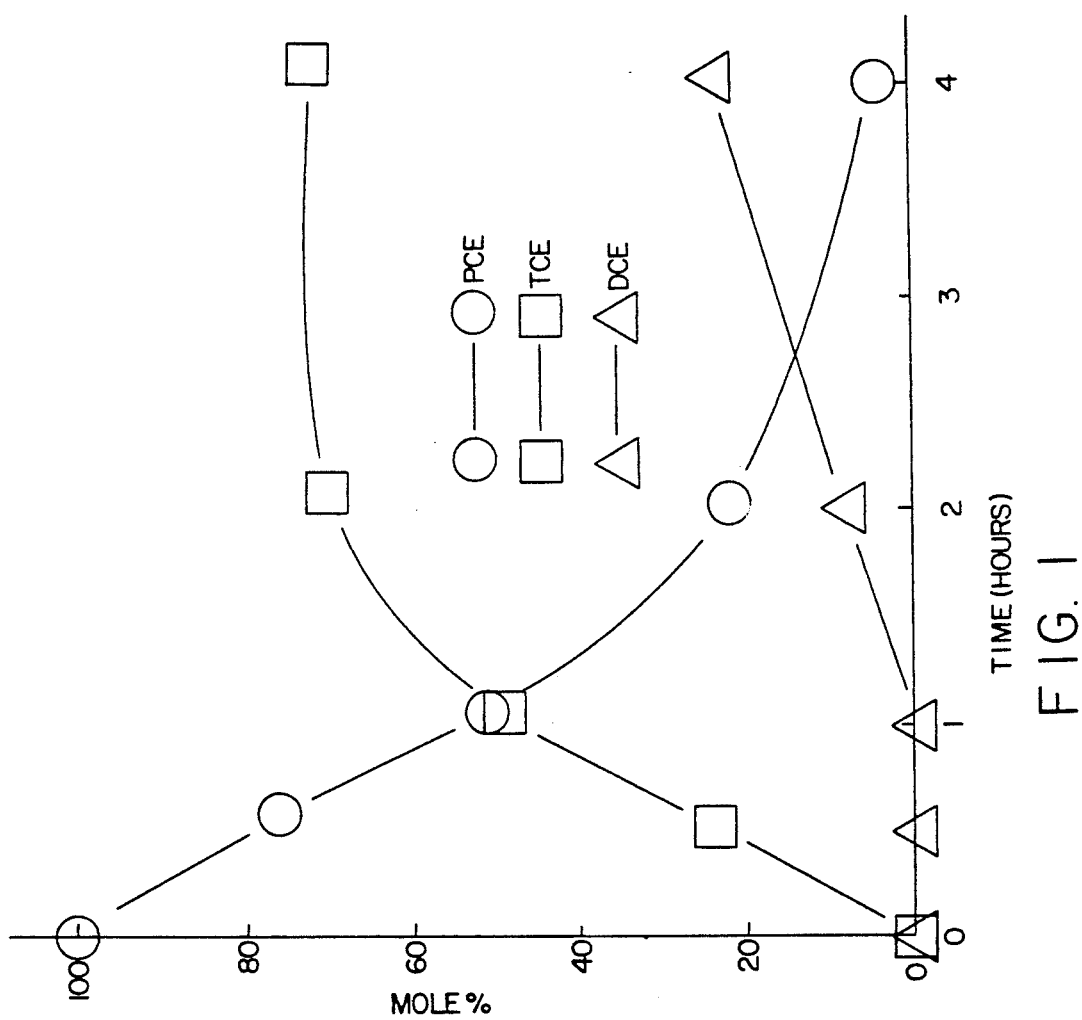

United States Patent [19]

Cole et al.

[11] Patent Number: 5,200,343
[45] Date of Patent: Apr. 6, 1993

[54] METHOD FOR MICROBIAL DEHALOGENATION OF HALOALIPHATIC COMPOUNDS USING A SULFATE REDUCING BACTERIA, DESULFOMONILE TIEDJEI

[75] Inventors: James R. Cole, East Lansing; Babu Z. Fathepure; James M. Tiedje, both of Lansing, all of Mich.

[73] Assignee: Board of Trustees operating Michigan State University, East Lansing, Mich.

[21] Appl. No.: 695,295

[22] Filed: May 3, 1991

[51] Int. Cl.$^5$ .............................. C12N 9/00; C12N 1/00
[52] U.S. Cl. .................................. 435/262.5; 435/243;
435/262; 435/821; 435/822
[58] Field of Search ....................... 435/262.5, 262, 243

[56] References Cited

PUBLICATIONS

Bhatnagar, L., et al., Biotechnology of Mixed Cultures, McGraw Hill pp. 293-340 (1991).
McCarty, P. L., In G. S. Omen (ed.), Environ. Biotechnology, pp. 143-162 (1988).
T. Vogel et al., Environ. Sci. Technol. 21: 722-736 (1987).
Shelton, D. R., et al., Appl. Environ. Microbiol. 48: 840-848 (1984).
Dolfing, J., Arch. Microbiol. 153: 264-266 (1990).
W. W. Mohn et al., Arch. Microbiol. 153: 267-271 (1990).
Dolfing, J., et al., Arch Microbiol. 149: 102-105 (1987).
Fathepure, B. Z., et al., Appl. Environ. Microbiol. 53: 2671-2674 (1987).
Suflita, J. M., et al., J. Ind. Microbiol. 3: 179-194 (1988).
Mohn, W. W. et al., Appl. Environ. Microbiol. 56: 1206-1211 (1990).
Stevens, T. O. et al., Appl Environ. Microbiol. 54: 2938-2943 (1988).
Stevens, T. O. et al., Appl. Environ. Microbiol. 54: 2944-2948 (1988).
Apajalahti, J., et al., Abstr. Ann Meet. Am. Soc. Microbiol., Q-36, p. 336 (1989).
DeWeerd, K. A., et al., Arch. Microbiol. 154: 23-30 (1990).
Mohn, W. W., J. Bacteriol. 172: 2065-2070 (1990).
Kramer, M., et al., Arch. Microbiol. 151: 232-237 (1987).
DeWeerd, K. A., et al., FEMS Microbiol. Ecol. 38: 331-339 (186).
Linkfield, T. G., et al., J. Indust. Microbiol. 5: 9-16 (1990).
Hanson, R. S. et al, In P. Gerhardt (ed.) Manual of methods for general Microbiol. Am. Soc. for Microbiol. Washington, D.C. pp. 328-364 (1981).
Bouwer, E. J., et al., Appl. Environ. Microbiol. 45: 1286-1294 (1983).
Hollinger, C., et al., Astr. Ann. Meet. Am. Soc. Microbiol., Q-49, p. 296 (1990).
Krone, U. E., et al., Biochemistry 28: 10061-10065 (1989).
Krone, U. E., et al., Biochemistry 28: 4908-4914 (1989).
Wood, J. M. et al., Biochemistry 7: 1707-1713 (1968).
Nelson, M. J., et al., Appl. Environ. Microbio. 53: 9490954 (1987).
Tsien, H. C., et al., Appl. Environ. Microbiol. 55: 3155-3161 (1989).
Wackett, L. P. et al., Appl. Environ. Microbiol. 55: 2960-2964 (1989).

*Primary Examiner*—Douglas W. Robinson
*Assistant Examiner*—Sandra Saucier
*Attorney, Agent, or Firm*—Ian C. McLeod

[57] ABSTRACT

An improved method for the degradation of haloaliphatic compounds using induced cells of sulfate reducing anaerobic bacterium, particularly *Desulfomonile tiedjei*, is described. The cells are induced using 1,3-substituted phenyl compounds, particularly 3-halobenzoates, such as 3-fluorobenzoate which are gratuitous inducers and thus are not dehalogenated. The result is a much more rapid dehalogenation of the haloaliphatic compounds than was achieved by prior art methods using uninduced cells.

10 Claims, 3 Drawing Sheets

METHOD FOR MICROBIAL DEHALOGENATION OF HALOALIPHATIC COMPOUNDS USING A SULFATE REDUCING BACTERIA, DESULFOMONILE TIEDJEI

BACKGROUND OF THE INVENTION (1) Field of the Invention

The present invention relates to a method for the dehalogenation of haloaliphatic compounds using preinduced cells of *Desulfomonile tiedjei* or other sulfate reducing anaerobes In particular, the present invention relates to the degradation of tetrachloroethylene (perchloroethylene; PCE) and trichloroethylene (TCE) which are persistent environmental contaminants occurring in waste sites and groundwater.

(2) Prior Art

Contamination of groundwater by halogenated, particularly chlorinated, aliphatic hydrocarbons has led to concern over their environmental fate. Many of these compounds, including tetrachloroethylene (PCE), are anaerobically dechlorinated in the natural environment and by both methanogenic and sulfate reducing enrichment cultures as discussed by Bhatnagar and Fathepure (Bhatnagar, L., and B. Z. Fathepure, In J. G. Zeikus and E. Johnson (ed.) Biotechnology of Mixed Cultures, McGraw Hill, p.293-340 (1991); McCarty, P. L., In G. S. Omen (ed.), Environmental Biotechnology, p.143-162 (1988); and Vogel, T. M., C. S. Criddle and P. L. McCarty, Environ. Sci. Technol. 21:722-736 (1987)). The anaerobic dechlorination of PCE is of special interest since, unlike trichloroethylene (TCE) and lower substituted ethylenes, PCE is apparently not attacked by aerobic microorganisms. Little is known, however, about either the bacteria molecular mechanism involved in the reaction.

*Desulfomonile tiedjei* strain DCB-1 was originally isolated from an anaerobic enrichment growing on 3-chlorobenzoate (Shelton, D. R. and J. M. Tiedje, Appl. Environ. Microbiol. 48:840-848 (1984)). *D. teidjei*, a sulfate reducing bacterium, can obtain energy by using 3-chlorobenzoate as an alternate electron acceptor, producing benzoate and HCl as products (Dolfing, J., Arch. Microbiol. 153:264-266 (1990); Dolfing, J. and J. M. Tiedje, Arch. Microbiol. 149:102-105 (1987); Mohn, W. W. and J. M. Tiedje, Arch. Microbiol. 153:267-271 (1990)). Interestingly, *D. teidjei* was also found to dechlorinate PCE. In one recent study, *D. teidjei* produced significant PCE dechlorination among several pure cultures of anaerobes tested (Fathepure, B. Z., et al., Appl. Environ. Microbiol. 53:2671-2674 (1987)). Dechlorination of PCE by *D. teidjei* was found to be 2.34 μmolg protein$^{-1}$ day$^{-1}$ by Fathepure et al. (Fathepure, B. Z., et al., Appl. Environ. Microbiol. 53:2671-2674 (1987)), and 4 μmol/l in five (5) months by Suflita et al. (Suflita, J. M., et al., J. Ind. Microbiol. 3:179-194 (1988)). These rates are slow.

OBJECTS

It is therefore an object of the present invention to provide a method for the relatively rapid dehalogenation by haloaliphatic hydrocarbons by sulfate reducing, anaerobic bacteria. Further, it is an object of the present invention to provide a method which is relatively simple and economical. These and other objects will become increasingly apparent by reference to the following description and the drawings.

In the Drawings

FIG. 1 is a graph showing the time course of PCE dechlorination. Suspensions were amended with PCE to a final concentration of 1.66 g/ml and duplicate vials harvested at the indicated times. The averages of duplicate vials are presented as the Mole percent (%) of recovered material. Suspensions contained 193 μg protein/ml.

Figure 2:
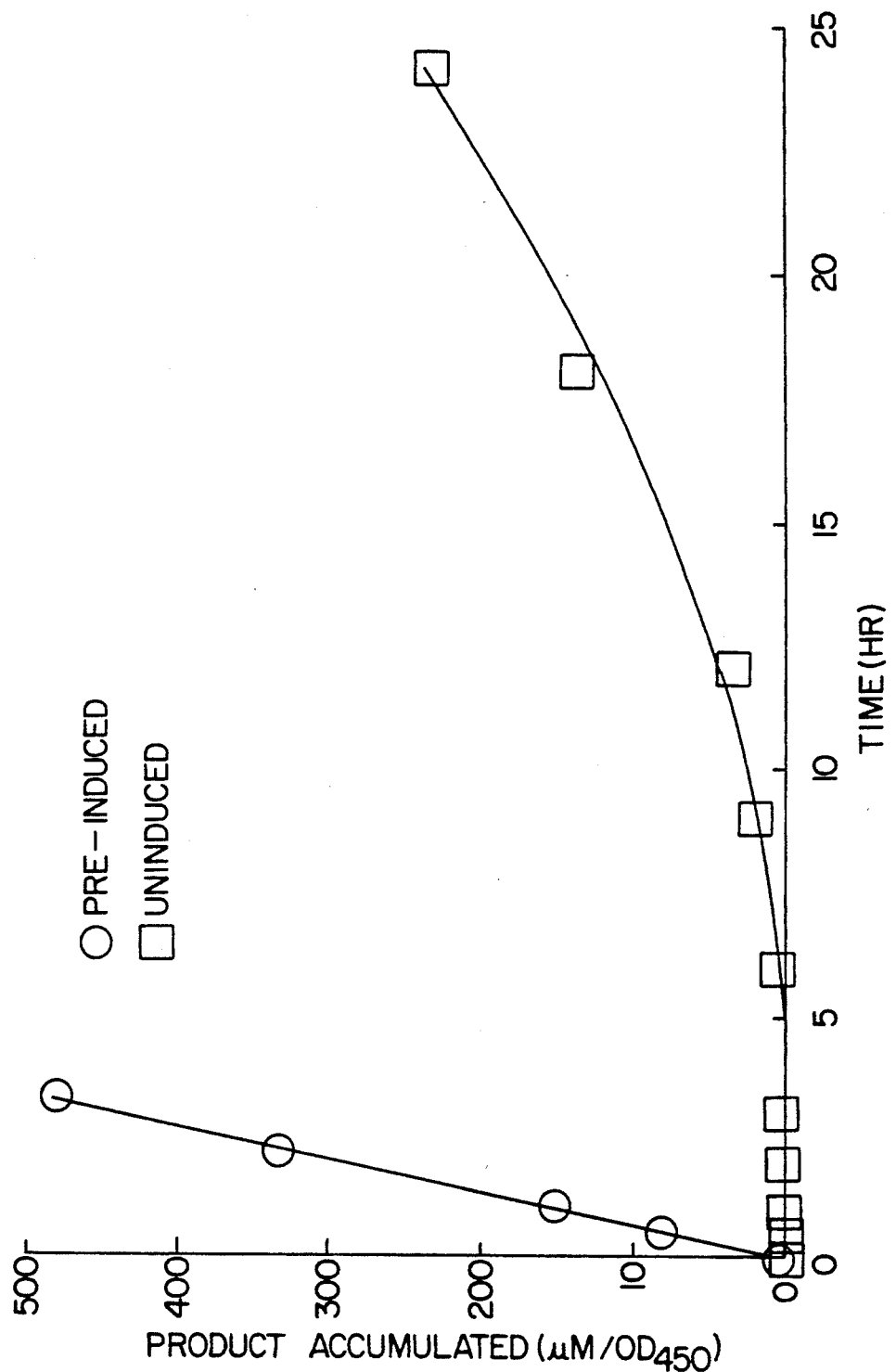

FIG. 2 is a graph showing dechlorination of 3,4-dichlorobenzoate on late log cultures grown with or without 3-chlorobenzoate. Triplicate cultures were grown with or without 3-chlorobenzoate and while the cultures were still growing they were fed 100 μM 3,4-dichlorobenzoate (a known substrate). The cultures were sampled at intervals and analyzed by HPLC for 4-chlorobenzoate accumulation.

Figure 3:
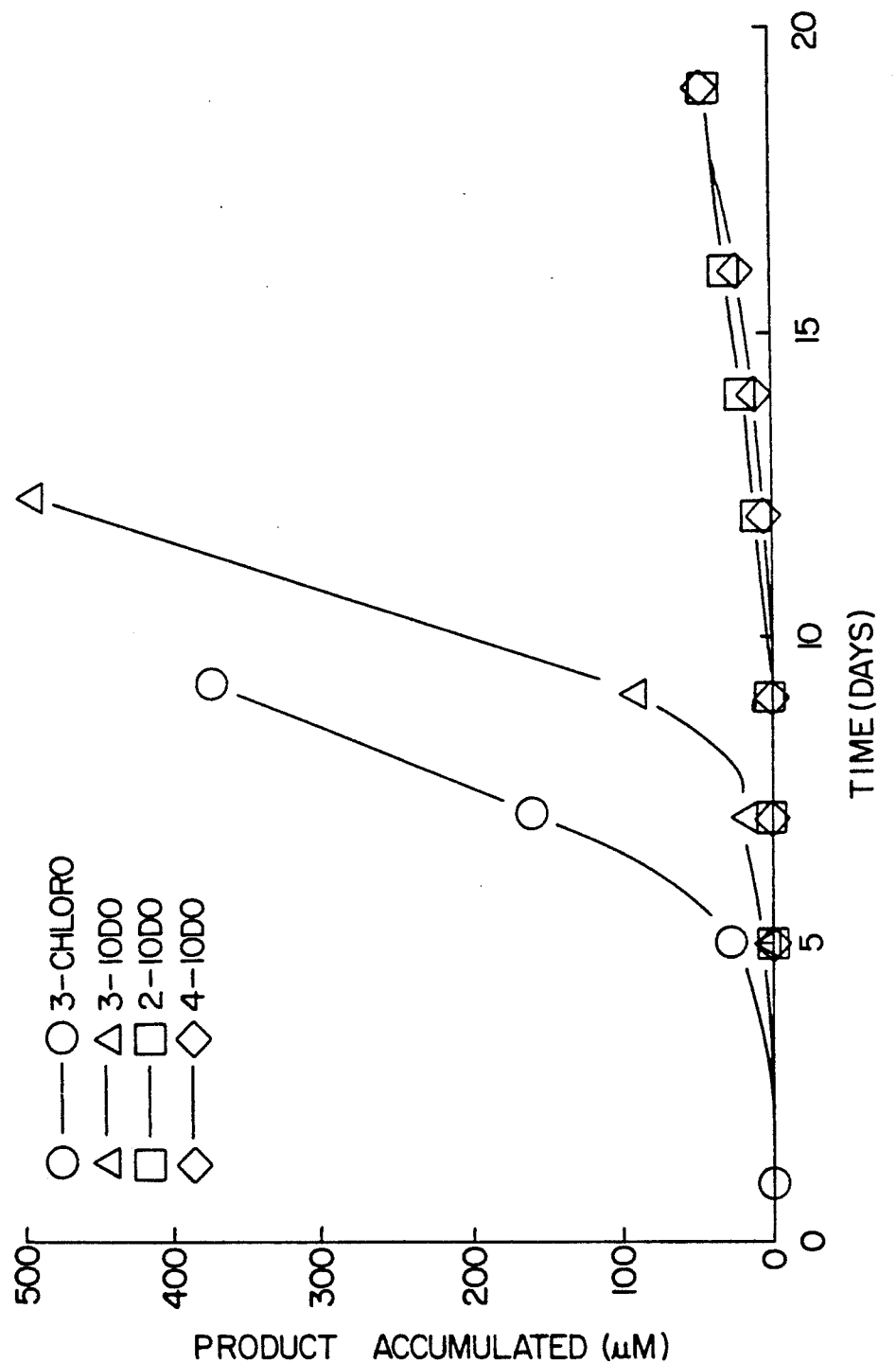

FIG. 3 is a graph showing dehalogenation of various halobenzoates during growth. Uninduced cultures were diluted 100 fold into fresh media supplemented with the indicated halobenzoate at 500 μM. Samples were harvested at indicated intervals and analyzed by HPLC for benzoate accumulation. Values presented are the average of triplicate cultures.

GENERAL DESCRIPTION

The present invention relates to a method for dehalogenation of a haloaliphatic compound wherein the halogen is selected from the group consisting of chlorine, bromine and iodine which comprises: growing cells of a sulfate reducing bacterium in the presence of a 1,3-substituted phenyl compound which induces the dehalogenation by the bacterium wherein the cells are grown under anaerobic conditions in a minimal growth medium for the cells, a carbon source, essential vitamins and minerals to provide induced cells with an ability to dehalogenate the compound; and anaerobically transferring the induced cells into a second medium containing the haloaliphatic compound so as to dehalogenate the haloaliphatic compound.

Further, the present invention relates to a bacterium which is *Desulfomonile tiedjei* ATCC 55165 which has been grown in a minimal medium containing a carbon source, minerals, essential vitamins and in addition a 1,3-substituted phenyl compound which induces dehalogenation by the bacterium as an essential ingredient and which bacterium is capable of dehalogenating a haloaliphatic compound wherein the halogen is selected from the group consisting of bromine, iodine and chlorine.

The carbon source is preferably selected from pyruvic acid pyruvic esters, and salts of pyruvic acids an mixtures thereof. Sodium pyruvate is preferred. Other carbon sources can be used such as 3-chlorobenzoate.

A reductant compound is provided in the growth media which is preferably selected from cysteine, sodium sulfate and titanium citrate.

The cells require vitamins for dechlorination activity. 1,4-Naphthoquinone, thiamine, and nicotinamide ar regarded as essential. They appear to be required for dechlorination and not for growth.

The 1,3-substituted phenyl compound as an inducer is preferably a meta substituted benzoate selected from the group consisting of m-fluorobenzoate, m-methylbenzate, m-trifluoromethyl benzoate, m-chlorobenzoate, m-iodobenzoate and m-bromobenzoate. The inducer can e selected from the group consisting of 3-chlorobenzylamine, 3-chlorobenzyl alcohol, 3-methylbenzylamine and 3-methylbenzyl alcohol. The gratuitous inducers are preferred (3-fluorobenzoate) since they are not themselves metabolized by the cells.

Besides PCE or TCE, other haloaliphatic compounds which are likely to be degraded are, carbon tetrachloride, chloroform, trichloroacrylic acid, particularly halogenated lower aliphatic compounds containing 1 to 8 carbon atoms.

D. tiedjei has been deposited with the American Type Culture Collection (ATCC) in Rockville, Maryland, under the Budapest Treaty, as ATCC No. 55165. A parallel deposit is ATCC 49306.

A unique morphological feature of D. teidjei is a collar which girdles each cell. This collar consists of a region where the cell wall folds over itself (Shelton, D. R., et al., Appl. Environ. Microbiol. 48:840–848 (1984)). The collar is the origin of polar cell growth and cell division (Mohn, W. W., et al., Appl Environ. Microbiol. 56:1206–1211 (1990)).

Mixed Cultures

Other anaerobes can be used with D. teidjei to facilitate the degradation of the byproducts from the initial dehalogenation by this strain Such anaerobes are for instance methanogenic and benzoate degrading anaerobes. After the initial anaerobic dehalogenation, aerobic bacteria can also be used to facilitate the mineralization of the byproducts of the halogenated hydrocarbon.

General Physiology

Initially D. teidjei could only be cultured on an undefined medium including rumen fluid, and pyruvate was the only substrate found to significantly support growth (Shelton, D. R. and J. M. Tiedje, Appl. Environ. Microbiol. 48:840–848 (1984)). Thiosulfate was later found to stimulate growth suggesting that the organism might be a sulfate-reducing bacterium (Stevens, T. O., et al., Appl. Environ. Microbiol. 54:2938–2943 (1988)). Growth on pyruvate was found to be mixotrophic, involving $CO_2$ fixation (Stevens, T. O., et al., Appl. Environ. Microbiol. 54:2944–2948 (1988)). Identification of vitamins stimulatory to D. teidjei (Apajalahti, J., et al., Abstr. Ann. Meet. Am. Soc. Microbiol., Q-36, p. 336 (1989); and DeWeerd, K. A., et al., Arch. Microbiol. 154:23–30 (1990)) has permitted studies using defined media which have greatly improved knowledge of the metabolic characteristics of this organism.

D. teidjei exploits several catabolic electron acceptors. The organism is a bona fide sulfate-reducing bacterium (Mohn, W. W., J. Bacteriol. 172:2065–2070 (1990)), having the usual ability to reduce sulfate or thiosulfate to sulfide (Equations 1 and 2):

$$4\ HCOOH + SO_4^= + H^+ \rightarrow 4\ CO_2 + HS^- + 4\ H_2O \quad (1)$$

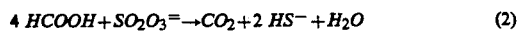

$$4\ HCOOH + S_2O_3^= \rightarrow 4\ CO_2 + 2\ HS^- + H_2O \quad (2)$$

D. teidjei has the additional ability, in the absence of a suitable electron donor, to gain energy from the disproportionation of thiosulfate to sulfide plus sulfate (Equation 3):

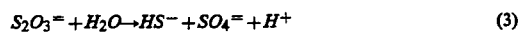

$$S_2O_3^= + H_2O \rightarrow HS^- + SO_4^= + H^+ \quad (3)$$

Growth by the latter lithotrophic fermentation is apparently possible for only a few of the sulfate reducers presently in pure culture (Kramer, M., et al., Arch. Microbiol. 151:232–237 (1989)). D. teidjei, like Desulfotomaculum spp. is more sensitive to sulfide than other sulfate reducers. Sulfide typically limits growth of D. teidjei on sulfur compounds in batch cultures and sulfide production is usually less than 3 mM (Mohn, W. W., J. Bacteriol. 172:2065–2070 (1990)). This sensitivity would select against D. teidjei during routine enrichment and isolation of sulfate reducers and may contribute to the lack of similar isolates.

D. teidjei also grows by an unusual fermentation of pyruvate plus $CO_2$ (Mohn, W. W., J. Bacteriol. 172:2065–2070 (1990)). The fermentation involves the oxidation of pyruvate to acetate plus $CO_2$ (Equation 4) and the reduction of $CO_2$ to acetate (Equation 5), with the oxidative and reductive processes balancing one another (Equation 6):

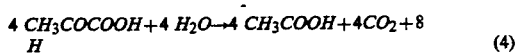

$$4\ CH_3COCOOH + 4\ H_2O \rightarrow 4\ CH_3COOH + 4CO_2 + 8H \quad (4)$$

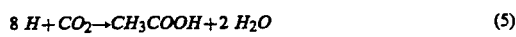

$$8\ H + CO_2 \rightarrow CH_3COOH + 2\ H_2O \quad (5)$$

$$4\ CH_3COCOOH + 2\ H_2O \rightarrow 5\ CH_3COOH + 2\ CO_2 \quad (6)$$

In many respects this resembles the terminal steps in homoacetogenic fermentation of sugars; however, D. teidjei is unable to use sugars. Like homoacetogens, D. teidjei has carbon monoxide dehydrogenase activity and is believed employ the acetyl-CoA pathway for $CO_2$ reduction. Unlike many homoacetogens, D. teidjei cannot grow on $H_2$ plus $CO_2$ or formate plus $CO_2$.

Reductive dehalogenation is yet another reaction exploited by D. teidjei for energy metabolism. Dolfing and Tiedje (Dolfing, J. and J. M. Tiedje, FEMS Microbiol. Ecol. 38:293–298 (1986)) constructed a defined consortium including D. teidjei which used 3-chlorobenzoate (3CB) as a sole substrate. Growth of the consortium was stimulated by dechlorination (Dolfing, J., et al., Arch. Microbiol. 149:102–105 (1987)). Subsequently, dechlorination was found to stimulate growth of D. teidjei in pure culture (Dolfing, J., Arch. Microbiol. 153:264–266 (1990); Mohn, W. W., et al., Arch. Microbiol. 153:267–271 (1990)). Dechlorination was coupled to formate oxidation (FIG. 9), or, probably, $H_2$ oxidation (Mohn, W. W., et al., Arch. Microbiol 153:267–271 (1990).

The coupling of dehalogenation to formate or $H_2$ oxidation suggests that energy conservation is via a respiratory process, since neither formate or $H_2$ is known to support substrate-level phosphorylation Like other sulfate reducers, D. teidjei appears to have several respiratory electron carriers Desulfoviridin and cytochrome c3 were isolated from D. teidjei (DeWeerd, K. A., et al., Arch. Microbiol. 154:23–30 (1990)). Naphthoquinone (or menadione) is required by D. teidjei for dehalogenation but not for fermentative growth. It is not reported whether the vitamin is also required by D. teidjei for sulfoxy anion metabolism; although the vitamin stimulates growth on pyruvate plus thiosulfate (DeWeerd, K. A., et al., Arch. Microbiol. 154:23–30 (1990)). In addition to their probable role in sulfate reduction, some or all of the above electron carriers may participate directly in dehalogenation or in respiratory energy conservation from dehalogenation.

Dechlorination directly supported ATP synthesis in stationary phase cultures which were limited by 3-chloro-benzoate (Dolfing, J., Arch. Microbiol. 153:264–266 (1990)) and in cell suspensions. In the latter system, the effects of uncouplers and ionophores suggest the involvement of a proton-motive force in the coupling of dechlorination and ATP synthesis. Additionally, the effects of N,N'-dicyclohexylcarbodiimide (DCCD), a proton-driven ATPase inhibitor, and of imposed pH gradients suggest the involvement of a proton-driven ATPase in the coupling of the processes. The evidence is consistent with chemiosmotic coupling of dechlorination and ATP synthesis, a novel respiratory process.

*D. tiedjei* appears to have a relatively limited range of electron donors In addition to pyruvate, formate and $H_2$ mentioned above, *D. teidjei* oxidizes CO, lactate, butyrate (Mohn, W. W., et al., J. Bacteriol. 172:2065-2070 (1990)) 3- and 4-methoxy benzoates and their derivatives, and benzoate (DeWeerd, K. A., et al., Arch. Microbiol. 154:23-30 (1990)). Acetate appears to be used, but only slowly (DeWeerd, K. A., et al., Arch. Microbiol. 154:23-30 (1990); Mohn, W. W., et al., J. Bacteriol. 172:2065-2070 (1990)). Oxidation of methoxy benzoates is via 0-demethylation to corresponding hydroxy benzoates (DeWeerd, K. A., et al., FEMS Microbiol. Ecol. 38:331-339 (1986)) which are not further degraded (Mohn, W. W., et al., J. Bacteriol. 172:2065-2070 (1990)). The latter activity is characteristic of organisms with the acetyl-CoA pathway. The electron donor range of *D. teidjei* is typical of sulfate reducing bacteria, and could allow *D. teidjei* a terminal position in anaerobic food chains, using products of fermentative organisms.

Induction of Dehalogenation

Initially it was reported that dehalogenation activity in *D. teidjei* was dependent on growth in the presence of 3CB (Shelton, D. R., and Tiedje, J. M., Appl. Environ. Microbiol. 48:840-848 (1984); and DeWeerd, K. A., et al., Abstr. Ann. Meet. Am. Soc. Microbiol., Q-43, p. 295 (1989)). More recently m-halobenzoates or analogs were also found to specifically induce dehalogenation activity. There are a number of inducers which are not substrates (gratuitous) as well as a number of substrates which are not inducers. Inducers must be meta-substituted, but dehalogenation activity can also act at the ortho and para positions. Inducers can have certain meta-substituents which are not transformed (e.g., F, $CH_3$, $CF_3$). If the lack of induction by certain substrates is common to other dehalogenating organisms, the failure to detect activity is not proof that such organisms are not present. Thus, dehalogenating organisms could possibly be undetected in experiments using current methodology

Inhibition of Dehalogenation by Sulfoxy Anions

The relationship between dehalogenation and metabolism of sulfoxy anions by *D. teidjei* is not simple. Thiosulfate and sulfite inhibit dechlorination of 3CB by growing cells (DeWeerd, K. A., FEMS Microbiol. Ecol. 38:331-339 (1986); Linkfield, T. G., et al., J. Indust. Microbiol 5:9-16 (1990)) and by resuspended cells (DeWeerd, K. A., et al., Arch. Microbiol. 154:23-30 (1990)). Sulfate inhibited dechlorination of 3CB by cells growing on one medium (Linkfield, T. G., et al., J. Indust. Microbiol. 5:9-16 (1990)) but not by cells growing on a different medium or by resuspended cells (DeWeerd, K. A., et al., Arch. Microbiol. 154:23-30 (1990)). The latter authors found that both 3CB and sulfoxy anions could support $H_2$ consumption by resuspended cells, the latter at a higher rate. With both electron acceptors present an intermediate rate of $H_2$ consumption was observed, suggesting to these authors that dechlorination and sulfoxy anion reduction are enzymatically distinct pathways which compete for limited electron donors. The above results suggest that inhibition of dehalogenation by thiosulfate and sulfite observed in undefined cultures may occur via intraspecific channelling of electrons to the different electron acceptors.

Taxonomy

DeWeerd et al (DeWeerd, K. A., et al., Arch. Microbiol. 154:23-30 (1990)) determined the 16S rRNA sequence of *Desulfomonile tiedjei* which clearly indicates that the organism is a member of the delta subdivision of the class Proteobacteria (purple bacteria). The degree of distance between *D. teidjei* and *Desulfovibrio desulfuricans* was greater than between *D. teidjei* and *Desulfuromonas acetoxidans* (an elemental sulfur-reducing bacterium) or Desulfobacter spp. It was concluded from the 16S rRNA sequence that *D. teidjei* represents a new genus among the sulfate-reducing bacteria. However, comparisons were only made with three other sulfate reducers, and the phylogenetic position of *D. teidjei* within that group remains unclear. The unique physiological characteristics of *D. teidjei* (above) and the sequence analysis led DeWeerd et al to assign the name, *Desulfomonile tiedjei* gen. nov. and sp. nov., to the organism, formerly strain DCB-1.

Syntrophy

Studies of *D. teidjei* suggest possible reasons why reductive dehalogenation is favored in undefined communities. In natural habitats *D. teidjei* appears to obtain a number of nutrients and other factors from other organisms. First, as an obligate anaerobe, *D. teidjei* requires a reduced oxygen-free environment created by other organisms. As mentioned above, *D. teidjei* uses electron donors which probably originate as end products of other anaerobes. Products of *D. teidjei* which are toxic to the organism, such as sulfide and benzoate, may be removed by other organisms. Five vitamins are stimulatory or, possibly, required by *D. teidjei* (DeWeerd, K. A., et al., Arch. Microbiol. 154:23-30 (1990)). Initially, *D. teidjei* required rumen fluid for growth and dehalogenation activity (Shelton, D. R., et al., Appl. Environ. Microbiol. 48:840-848 (1984)). It was later found that fermentative growth could occur in a defined medium but that dehalogenation activity required a factor which could be provided by rumen fluid, a Propionibacterium sp. in coculture or the culture fluid of the Propionibacterium sp. (J. Apajalahati, J. Cole, J. Tiedje, Abstr. Ann. Meet. Am. Soc. Microbiol., Q-43, p. 295 (1989)). The factor in the culture fluid was extractable and its chemical properties suggested that it was a quinoid compound. The factor could be replaced by 1,4-naphthoquinone or menadione (vitamin $K_3$). Thus, *D. teidjei* conforms to the general rule of syntrophy in anaerobic ecosystems. A consequence of such interdependence may be the observed difficulty of isolating other dehalogenating organisms. Successful applications of biological reductive dehalogenation will likely require the use and understanding of these complex anaerobic communities.

SPECIFIC DESCRIPTION

Example 1

For these experiments 3-chlorobenzoate dechlorination activity was induced with 3-fluorobenzoate, an efficient gratuitous inducer of halobenzoate dehalogenation. Since 3-fluorobenzoate is not transformed by DCB-1, co-induction was tested without any metabolic changes (e.g. electron transport mediated respiration) that would occur during dechlorination of 3-chlorobenzoate and that might have some indirect effect on the rate of PCE dechlorination.

Cultures were grown using strict anaerobic technique in a synthetic minimal medium amended with vitamins (DeWeerd, et al, Arch. of Microbiol. 154, 23–30 (1990)), pyruvate at 20 mM, and reduced with 1 mM cysteine and 0.1 mM $Na_2S_2O_4$. The concentration of nicotinamide and 1,4-naphthoquinone were 500 $\mu gl^{-1}$ and 200 $\mu gl^{-1}$, respectively. Thiamine, hemin and lipoic acid were used at 50 $\mu g$/liter. To induce 3-chlorobenzoate dechlorination activity, 3-fluorobenzoate was added to 0.1 mM. The complete medium was inoculated with a 1% transfer from homologous medium (without fluorobenzoate). Cultures were grown at 37° C. in the dark for about 14 days for fresh cells or 28 days for starved stationary phase cells.

Cultures were harvested by centrifugation and resuspended in 20 to 40% of the initial volume in a cold anaerobic assay buffer normally consisting of 50 mM NaCl, 10 mM sodium pyruvate, 10 mM HEPES (N-2[hydroxyethylP]piperazine-N'-[2-ethanesulfonic acid], 28:10061–10065 (1989); Krone, U. E., et al., Biochemistry hemisodium salt Sigma);, 0.00001% resazurin and reduced with 1 mM cysteine-HCl and 1 mM titanium (III) citrate. Resuspended cells were used to completely fill $N_2$ sparged 10 ml serum bottles after which chlorinated ethylenes were added from a 0.5 or 1 mg/ml stock in methanol for PCE and TCE respectively. The vials were immediately sealed with Teflon lined rubber septa and aluminum crimp seals, leaving no headspace. The assays were commenced by transferring the serum bottles to a 37° C. water bath. The assays were terminated at the indicated times by transferring the serum bottles to an ice water bath, where they were stored until analyzed. Protein concentrations were determined by a modification of the Lowry method (Hanson, R. S. and J. A. Phillips, In P. Gerhardt (ed.) Manual of methods for general microbiology. American Society for Microbiology, Washington, D. C. p. 328-364 (1981)).

Chlorinated ethylenes were monitored with a Tekmar purge and trap unit (model 4000) connected to a Hewlett-Packard GC (Sunnyville, Calif.) equipped with an HP-5 cappillary column (30 m×0.53 mm×2.6 $\mu m$ film thickness) and flame ionization detector. Samples (5 ml) were purged onto Tenax TA (Supelco, Bellefonte, Pa.) adsorbent with helium (30 ml/min for 16 min.), desorbed (180° C. for 4 min.), and separated using helium as a carrier at 6 ml/min. The temperature program was 30° C. for 8 min, increasing to 200° C. at 4° C./min and followed by an isothermal period of 5 min. The injection and detector temperatures were 220° C. and 300° C., respectively. PCE and its dechlorinated products were identified by comparison with authentic standards.

Rapid transformation of PCE to TCE and cis-DCE (cis-dichloroethylene) occurred in mixtures (suspensions) with resuspended cells grown with 0.1 mM 3-fluorobenzoate, while no dechlorination was detected with uninduced mixtures (FIG. 1). Other experiments with a longer time course showed formation of small amounts of trans-DCE (trans-dichloroethylene) in addition to cis-DCE (see also Table 2).

To further examine the transformation of both PCE and TCE and to determine if dechlorination of TCE also requires induction, a similar experiment was conducted to measure the initial transformation rates of PCE and TCE (Table 1.). Only cultures pre-induced with 3-fluorobenzoate showed measurable product formation from either PCE or TCE, indicating that both activities require induction. The extent of transformation of PCE to TCE (43.8 mol g protein $^{-1}$ in 2H) was considerably faster than the rate of transformation of TCE to DCE (11 mol g protein $^{-1}$ in 2h), as expected from the redox potentials of these reactions (Vogel, T. M., et al., Environ. Sci. Technol. 21:722-736 (1987)) and results from mixed culture systems (Bouwer, E. J., and P. L. McCarty, Appl. Environ. Microbiol. 45:1286-1294 (1983)). The rate of transformation of PCE and TCE were much greater for the induced cultures than for the non-induced cultures.

Example 2

There are several reports of reductive dechlorination of chlorinated methanes, ethanes and ethylenes catalyzed by purified enzyme cofactors, often using a strong synthetic reductant (see e.g. Hollinger, C., et al., Abstr. Ann. Meet. Am. Soc. Microbiol., Q-49, p. 296 (1990); Klecka, G. M. and S. J. Gonsior, Chemosphere 13:391–402 (1984); Krone, U. E., et al., Biochemistry 28:10061–10065 (1989); Krone, U. E., et al., Biochemistry 28:4908–4914 (1989); Wod, J. M., et al., Biochemistry 7:1707-1713 (1968)). Although in our system dechlorination occurred only in pre-induced cultures, we were concerned that the dechlorination we were observing might not be mediated by living cells but instead by some factor(s) released only from damaged induced cells and perhaps involving the titanium (III) citrate reductant added to our buffer system.

The titanium (III) citrate in the buffer system was not required for PCE dechlorination since similar activity was obtained with sodium sulfide as the medium reductant (Table 2). Addition of formaldehyde to a final concentration of 0.2% almost totally blocked dechlorination, indicating that killed cells are not active in the dechlorination reaction (Table 2).

Example 3

A test was conducted to determine if dechlorination events depended on cellular production of electron donors, since it was found that dechlorination of 3-chlorobenzoate was stimulated by the addition of pyruvate in starved stationary phase cultures, but less stimulated in resuspended growing cells D. teidjei accumulates glycogen (Mohn, W. W., et al., Appl. Environ. Microbiol. 56:1206-1211 (1990)) and it was probable that this may act as an endogenous electron donor until depleted Using similarly starved cells, it was found that both PCE and 3-chlorobenzoate dechlorination were reduced by about the same factor in the absence of pyruvate compared to the presence of pyruvate (to about 12% for 3-chlorobenzoate dechlorination and to about 14% for PCE dechlorination) (Table 3). Taken together, these results indicate that metabolically active cells are required for PCE dechlorination.

It was found that induction of 3-chlorobenzoate dechlorination activity involves a lag consistent with the synthesis of new macromolecules (enzymes) necessary for dechlorination. Although 3-chlorobenzoate and PCE dechlorination might possibly involve separate enzyme systems that happen to co-induce, it seems more likely that both activities share at least one enzyme induced by 3-fluorobenzoate. Very little is known about the mechanism of PCE or chlorobenzoate dechlorination in *D. teidjei*. If both PCE and 3-chlorobenzoate dechlorination share the same "dechlorinase" enzyme then this information helps limit the plausible mechanisms for dechlorination. For example, partial ring hydrogenation by hydride ion addition para to the chlorine might make a reasonable intermediate for 3-chlorobenzoate dechlorination but is not a feasible mechanism for PCE dechlorination. If the same mechanism is responsible for the two dechlorination reactions then a mechanism such as direct nucleophilic attach on the Cl position or electrophilic addition would appear more likely.

The two previous studies examining dechlorination of PCE by *D. teidjei* reported much lower rates of PCE dechlorination than the present study (an apparent rate of 21.9 mol g protein$^{-1}$ hour$^{-1}$ in the present study versus 2.34 mol g protein $^{-1}$ day$^{-1}$ reported in Fathepure et al. (Fathepure, B. Z., et al., Appl. Environ. Microbiol. 53:2671-2674 (1987)); and 4 nmol/l in 5 months reported in Suflita et al. (Suflita, J. M., et al., J. Ind. Microbiol. 3:179-194 (1988)). This increased rate of dechlorination illustrates the improvements of the present invention. Since the less chlorinated ethylenes can be rapidly oxidized by aerobic microorganisms (see e.g. Nelson, M. J. K., et al., Appl. Environ. Microbiol. 53:949-954 (1987); Tsien, H. C., et al., Appl. Environ. Microbiol. 55:3155-3161 (1989); Vogel, T. M., et al., Environ Sci. Technol. 21:722-736 (1987); and Wackett, L. P., et al., Appl. Environ. Microbiol. 55:2960-2964 (1989)), the obligately anaerobic first dechlorination step is often rate limiting for PCE bioremediation efforts. Therefore, the rate increases reported here is important for PCE bioremediation.

TABLE 1

Rates of PCE and TCE dechlorination in induced and non-induced cells[a].

| Substrate | Induced | Mole % recovered[b] | | | Total Cl Removed[c] (μmol/ g prot. in 2 h) |
|---|---|---|---|---|---|
| | | PCE | TCE | cis-DCE | |
| PCE | + | 45.7 | 54.3 | 0.0 | 43.9 |
| | | (1.1) | (1.1) | (0.0) | (0.9) |
| | − | 100.0 | 0.0 | 0.0 | 0.0 |
| | | (0.0) | (0.0) | (0.0) | (0.0) |
| TCE | + | — | 89.2 | 10.8 | 11.0 |
| | | — | (0.3) | (0.3) | (0.3) |
| | − | — | 100.0 | 0.0 | 0.0 |
| | | — | (0.0) | (0.0) | (0.0) |

[a]Suspensions were amended with PCE or TCE to a final concentration of 2 μg/ml and incubated at 37° C. for 2 hr. Suspensions of induced and uninduced cells contained 149 and 153 μg protein per ml respectively.
[b]Data are presented as the average of duplicate vials with the sample standard deviation in parenthesis.
[c]Calculated from the input concentration of chlorinated ethylenes and the Mole % of recovered material.

TABLE 2

Effect of different medium reductants and sterilant on PCE dechlorination[a].

| Treatment | Mole % recovered[b] | | | | Total Cl Removed[c] (μmol/ g prot. in 2 h) |
|---|---|---|---|---|---|
| | PCE | TCE | cis-DCE | trans-DCE | |
| Reductant[b] | | | | | |
| TiCit | 0.0 | 9.4 | 85.8 | 4.7 | 50.0 |
| | (0.0) | (1.3) | (1.3) | (0.0) | (0.4) |
| Na$_2$S | 6.3 | 18.6 | 70.7 | 4.4 | 45.4 |
| | (2.6) | (0.2) | (2.4) | (0.1) | (1.4) |
| Formaldehyde[c] | | | | | |
| + | 95.0 | 5.0 | 0.0 | 0.0 | 1.0 |
| | (0.4) | (0.4) | (0.0) | (0.0) | (0.1) |
| − | 0.0 | 26.4 | 69.4 | 4.2 | 34.1 |

TABLE 2-continued

Effect of different medium reductants and sterilant on PCE dechlorination[a].

| Treatment | Mole % recovered[b] | | | | Total Cl Removed[c] (μmol/ g prot. in 2 h) |
|---|---|---|---|---|---|
| | PCE | TCE | cis-DCE | trans-DCE | |
| | (0.0) | (0.0) | (0.0) | (0.0) | (0.0) |

[a]In two separate experiments induced cultures were resuspended, amended with PCE to a final concentration of 1.66 μg/ml and incubated at 37° C. for 2 hours. Data are the average of duplicate vials and are presented as in Table 1.
[b]Cultures were resuspended in either the standard buffer with titanium (III) citrate (TiCit) to a concentration of 381 μg protein per ml or at a concentration of 372 μg protein per ml in buffer with 1 mM sodium sulfide (Na$_2$S) substituting for titanium (III) citrate.
[c]Cultures were resuspended at a concentration of 509 μg protein per ml in buffer containing 50 mM HEPES. Formaldehyde (37%) was added to a final concentration of 0.2% immediately before sealing two vials.

TABLE 3

Stimulation of dechlorination by pyruvate addition to starved stationary phase cells[a].

| Pyruvate | Mole % recovered[b] | | | |
|---|---|---|---|---|
| | PCE | TCE | cis-DCE | trans-DCE |
| +[b] | 2.1 | 44.1 | 50.3 | 3.5 |
| | (0.0) | (4.1) | (4.9) | (0.8) |
| − | 78.6 | 21.4 | 0.0 | 0.0 |
| | (1.3) | (1.3) | (0.0) | (0.0) |

| Pyruvate | Total Cl removed (μmol/g prot. in 2 h) | 3ClBz Cl removed[c] (μmol/g prot. in 1 h) |
|---|---|---|
| +[b] | 29.1 (0.8) | 255 (33) |
| − | 4.1 (0.3) | 30 (4) |

[a]Starved stationary phase induced cultures were resuspended at a concentration of 521 μg protein per ml in buffer without pyruvate, amended with PCE to a final concentration of 1.66 μg/ml and incubated at 37° C. for 2 hours. Data are the average of duplicate vials and are presented in Table 1.
[b]0.1 mMole sodium pyruvate was added to duplicate vials before addition of cell suspensions to give a final concentration of ca. 10 mM pyruvate.
[c]Parallel replicate vials amended with 3-chlorobenzoate to a final concentration of 500 μM were incubated for one hour and the dechlorinated benzoate product monitored by HPLC as previously described (Mohn, W. W. and J. M. Tiedje, Arch. Microbiol. 153:267-271 (1990)). data are presented (3-ClBz Cl removed) as Mole benzoate accumulated per g protein during the 1 hour incubation.

The following Examples 4 to 6 show various 1,3-substituted phenyl compounds used as inducers. The examples show the dehalogenation of 3-chlorobenzoate. The degradation of PCE and TCE is accomplished in the manner of Examples 1 to 3.

TABLE 4

Induction of 3-Chlorobenzoate Dechlorination Activity by Growth with 3-Chlorobenzoate or Various Analogues (nMol/hr/mg protein).

| Inducer Analogue | | Induction Activity |
|---|---|---|
| 1 Position | 3 Position | |
| No Analogue | | 0 ± 0 |
| —COOH | —Cl | 672 ± 8 |
| —COOH | —COH | 8 ± 1 |
| —COOH | —NH$_2$ | 4 ± 1 |
| —COOH | —CN | 7 ± 1 |
| —COOH | —OH | 3 ± 4 |
| —COOH | —CH$_3$ | 409 ± 6 |
| —COOH | —F | 570 ± 37 |
| —COOH | —CF$_3$ | 383 ± 6 |
| —CONH$_2$ | —Cl | 113 ± 27 |
| —CH$_2$OH | —Cl | 86 ± 5 |

Example 4

Substrate analogues were utilized to examine this induction and identify compounds that are good inducers of dechlorination activity but are not themselves transformed (gratuitous inducers). Additionally, we have found compounds (2- and 4-iodobenzoate) that are substrates for the dehalogenation reaction by pre-induced cells but are not inducers themselves.

The proteins accumulated in cells grown with and without 3-chlorobenzoate were examined and have found several differences. At the present time we are unable to assign a specific function to any of these proteins. In addition to dechlorination—specific proteins, some differences are likely due to changes in metabolism caused by chlorobenzoate acting as an electron acceptor. Use of the gratuitous inducers discussed above should allow us to differentiate between these possibilities.

Table 4. Cultures were grown in the presence of 3-chlorobenzoate or a 3-chlorobenzoate analogue substituted at the 1- or 3- position with the indicated functional groups. After several generations the culture were concentrated, washed and resuspended in anaerobic buffered salts containing 1 mM 3-chlorobenzoate and 10 mM pyruvate (as electron donor). Putative inducers were all at 500 µM except 3-formylbenzoate (100 µM, higher concentrations inhibited growth) and 3-chlorobenzoate (dechlorinated during growth, amended at intervals). After two hours samples were taken for benzoate analysis by HPLC. Values presented are the average of duplicate or triplicate cultures ± sample standard deviation.

All 3-halo compounds were tested as substrates using 3-fluorobenzoate induced cells. Assays were essentially as described above, with the halo analogues at 500 µM substituting for 3-chlorobenzoate. In addition to 3-chlorobenzoate, dehalogenation was detected only for 3-chlorobenzamide (116±27 nMol/hr/mg protein).

TABLE 5

Rates of Dehalogenation of Chloro- and Iodobenzoates by Pre-Induced cells and Induction of 3-Chlorobenzoate Dechlorination activity by Growth with Chloro- and Iodobenzoates. (nMol/hr/mg protein)

| Halobenzoate Tested | Dehalogenation Rate | Induction Activity |
|---|---|---|
| 2-chloro- | ND | 0 ± 0 |
| 3-chloro- | 358 ± 39 | 672 ± 8 |
| 4-chloro- | ND | 3 ± 5 |
| 2-iodo- | 38 ± 0.5 | 13 ± 9 |
| 3-iodo- | 40 ± 0.2 | 582 ± 59 |
| 4-iodo- | 52 ± 1.0 | 7 ± 10 |
| None | — | 6 ± 4 |

Example 5

Table 5. Chloro- and iodobenzoates were tested as inducers of 3-chlorobenzoate dehalogenation activity as described in the legend to Table 4. All compounds were initially at 500 µM; the 3-halo compounds were amended during growth as they were dehalogenated. Values presented are the average of duplicate or triplicate cultures± sample standard deviation.

Compounds were tested as substrates with 3-fluorobenzoate induced cells as described in the legend to Table 1. Values presented are the average of triplicate assays± sample standard deviation.

ND=not detected; product levels were not significantly above background.

TABLE 6

Dechlorination of 3-Chlorobenzoate in the Presence of Various Analogues by Induced Cells.

| Substrate Analogue | | |
|---|---|---|
| 1 Position | 3 Position | % of Control |
| —COOH | —H | 106 |

TABLE 6-continued

Dechlorination of 3-Chlorobenzoate in the Presence of Various Analogues by Induced Cells.

| Substrate Analogue | | |
|---|---|---|
| 1 Position | 3 Position | % of Control |
| —COOH | —NH$_2$ | 78 |
| —COOH | —CN | 76 |
| —COOH | —OH | 91 |
| —COOH | —CH$_3$ | 119 |
| —COOH | —F | 114 |
| —COOH | —CF$_3$ | 94 |
| —CONH$_2$ | —Cl | 100 |
| —CH$_2$OH | —Cl | 108 |

Example 6

Table 6. 3-fluorobenzoate induced cultures were washed and resuspended essentially as described in the legend to Table 6 with 100 µM 3-chlorobenzoate and the indicated analogues at 500 µM. Dechlorination rates were normalized to the rate in assays with no analogue to obtain the values presented.

The following conclusions were reached from Examples 4 to 6.

1) Dehalogenation by DCB-1 is inducible and induction of activity shows a lag consistent with the synthesis of new protein.

2) Some substrate analogues are gratuitous inducers and can induce dehalogenation activity in the absence of substrate turnover, e.g. 3-fluoro and 3-methyl-benzoate.

3) Dehalogenation activity is not limited to 3-halobenzoates 2 and 4-iodobenzoate do not induce dehalogenation activity but are dehalogenated by pre-induced cells. 3-Chlorobenzamide is both a substrate and inducer.

4) Several analogues, including some efficient gratuitous inducers, were tested as putative inhibitors of dechlorination. None of the analogues tested were effective inhibitors.

5) Several differences were seen in the proteins accumulated between uninduced and 3-chlorobenzoate grown cultures.

It is intended that the foregoing description be only illustrative of the present invention and that the present invention be limited only by the hereinafter appended claims.

We claim:

1. A method for dehalogenation of a haloaliphatic compound wherein the halogen is selected from the group consisting of chlorine, bromine and iodine which comprises:

(a) growing cells of a sulfate reducing bacterium having the sulfate reducing and dehalogenation characteristics of *Desulfomonile tiedjei* ATCC 55165 in the presence of a 1,3-substituted phenyl compound which induces the dehalogenation by the bacterium without being metabolized wherein the cells are grown under anaerobic conditions in a synthetic chemically defined medium for the cells consisting essentially of, a pyruvic compound as an electron donor selected from the group consisting of pyruvic acid, pyruvic esters, acid salts of pyruvic acids and mixtures thereof, 1,4-naphthoquinone, thiamine and nicotinamide, essential vitamins and minerals to provide induced cells with an ability to dehalogenate the haloaliphatic compound; and (b) anaerobically transferring the induced cells into a second chemically defined medium containing the haloaliphatic compound so as to dehalogenate the haloaliphatic compound.

2. The method of claim 1 wherein the first and second growth media in steps (a) and (b) contain the pyruvic compound.

3. The method of claim 2 wherein the pyruvic compound in steps (a) and (b) is sodium pyruvate.

4. The method of claim 1 wherein the haloaliphatic compound is selected from the group consisting of perchloroethylene and trichloroethylene.

5. The method of claim 1 wherein the defined media in steps (a) and (b) contains a reductant compound selected from the group consisting of cysteine, sodium sulfate and titanium citrate.

6. The method of claim 1 wherein the halogen in the haloaliphatic compound is chlorine.

7. The method of claim 1 wherein the 1,3-substituted phenyl compound is m-fluorobenzoate, m-methylbenzoate and m-trifluoromethyl benzoate.

8. The method of claim 1 wherein the 1,3-substituted phenyl compound is m-fluorobenzoate.

9. The method of claim 1 wherein the 1,3-substituted phenyl compound is selected from the group consisting of 3-chlorobenzylamine, 3-chlorobenzyl alcohol, 3-methylbenzylamine and 3-methylbenzyl alcohol.

10. The method of claim 1 wherein the bacterium is *Desulfomonile teidjei* deposited as ATCC 55165.

* * * * *

UNITED STATES PATENT AND TRADEMARK OFFICE
CERTIFICATE OF CORRECTION

PATENT NO. : 5,200,343  
DATED : April 6, 1993  
INVENTOR(S) : James R. Cole, Babu Z. Fathepure and James M. Tiedje It is certified that error appears in the above-identified patent and that said Letters Patent is hereby corrected as shown below:

Title page, column 2, line 7, "331-339 (186)" should be --331-339 (1986)--.

Title page, column 2, line 15, "Astr. Ann. Meet." should be --Abstr. Ann. Meet.--.

Title page, column 2, line 17, the following reference should be included --Klecka, G. M., et al., Chemosphere 13:391-402 (1984))--.

Column 1, line 12, a period --.-- should be inserted after "anaerobes" and before "In".

Column 1, line 36, after "bacteria", the following should be inserted --responsible for the anaerobic dechlorination of PCE or the--.

Column 2, line 51, a comma --,-- should be inserted after "pyruvic acid".

Column 2, line 51, "an" should be --and--.

Column 2, lines 63 and 64, "m-methylbenzate" should be --m-methylbenzoate--.

UNITED STATES PATENT AND TRADEMARK OFFICE
CERTIFICATE OF CORRECTION

PATENT NO. : 5,200,343
DATED : April 6, 1993
INVENTOR(S) : James R. Cole, Babu Z. Fathepure and James M. Tiedje It is certified that error appears in the above-identified patent and that said Letters Patent is hereby corrected as shown below:

Column 2, line 66, "e selected" should be --be selected--.

Column 3, line 11, the heading --Morphology/cell division-- should be inserted before the paragraph beginning "A unique morphological feature".

Column 3, line 23, a period --.-- should be inserted after "strain" and before "Such".

Column 3, line 54 "4 HCOOH + $SO_2O_3$ = → $CO_2$ + $HS^-$ + $H_2O$" should be --4 HCOOH + $S_2O_3$ = → $4CO_2$ + 2 $HS^-$ + $H_2O$--.

Column 4, line 26, after "believed", --to-- should be inserted.

Column 4, line 47, a period --.-- should be inserted after "phosphorylation" and before "Like".

Column 4, line 49, a period --.-- should be inserted after "carriers" and before --Desulfoviridin--.

Column 5, line 9, a period --.-- should be inserted after "donors" and before --In--.

Column 5, line 48, a period --.-- should be inserted after "methodology".

Column 7, line 46, "cappillary" should be --capillary--.

UNITED STATES PATENT AND TRADEMARK OFFICE
CERTIFICATE OF CORRECTION

PATENT NO. : 5,200,343
DATED : April 6, 1993
INVENTOR(S) : James R. Cole, Babu Z. Fathepure and James M. Tiedje It is certified that error appears in the above—identified patent and that said Letters Patent is hereby corrected as shown below:

Column 8, line 8, "(11 mol g" should be --11 $\mu$mol g--.

Column 8, line 28, "Wod" should be --Wood--.

Column 8, line 52, a period --.-- should be inserted after "depleted" and before "Using".

Column 9, lines 17 and 18, "21.9 mol g protein" should be --21.9 $\mu$mol g protein-- and "2.34 mol g" should be --2.34 $\mu$mol g--.

Column 12, line 33, a period --.-- should be inserted after "benzoates" and before "2".

Signed and Sealed this

Twenty-second Day of February, 1994

Attest:

BRUCE LEHMAN

Attesting Officer

Commissioner of Patents and Trademarks